United States Patent [19]

Binder et al.

[11] Patent Number: 5,431,933
[45] Date of Patent: Jul. 11, 1995

[54] ANIMAL FEED SUPPLEMENT BASED ON A FERMENTATION BROTH AMINO ACID, A PROCESS FOR ITS PRODUCTION AND ITS USE

[75] Inventors: Wolfram Binder, Rodenbach; Heinz Friedrich, Hanau; Hermann Lotter, Hainburg; Herbert Tanner, Hanau; Henning Holldorff, Altenstadt; Wolfgang Leuchtenberger, Bielefeld, all of Germany

[73] Assignee: Degussa Aktiengesellschaft, Frankfurt, Germany

[21] Appl. No.: 946,069

[22] Filed: Sep. 17, 1992

[30] Foreign Application Priority Data

Sep. 17, 1991 [DE] Germany .................. 41 30 868.9

[51] Int. Cl.⁶ .................. A23J 3/20; A23K 1/00; C12P 13/04
[52] U.S. Cl. .................. 426/60; 426/2; 426/656; 435/106
[58] Field of Search .................. 426/60, 61, 656, 69; 435/106, 115

[56] References Cited

U.S. PATENT DOCUMENTS 5,133,976  7/1992  Rouy .

FOREIGN PATENT DOCUMENTS

| 0122163 | 3/1984 | European Pat. Off. . |
| 2556230 | 12/1983 | France . |
| 2640640 | 12/1988 | France . |
| 2676234 | 11/1992 | France . |
| 2357119 | 11/1973 | Germany . |
| 139205 | 12/1979 | Germany . |
| 2231335 | 10/1988 | United Kingdom . |
| 1358898 | 12/1987 | U.S.S.R. . |

OTHER PUBLICATIONS

European Search Report.
Document in German from Synopse 1944 entitled "Aufabeitung either Aminosaure-Losung-Untersuchungen Zum . . . " by Detlef Schartges et al. Chem.-Ing.-Tech. 63 (1991) Nr. 4, S. 390–391.
Japanese Abstract J56085291 entitled "Tryptophan Produce Microorganism React . . . " 4 pages.
Japanese Abstract J61200949 entitled "Concentrate Amino Acid Pass Buffer Aqueous . . . "5 pags.
Chemical Abstracts, vol. 115:181567b (1991) by Kaiho, Yasunori entitled "Isolation of Tryptophan from fermentation broth by decanting centrifuges."

Primary Examiner—Donald E. Czaja
Assistant Examiner—Curtis E. Sherrer
Attorney, Agent, or Firm—Cushman Darby & Cushman

[57] ABSTRACT

An animal feed supplement and processes for its production which provide an inexpensive, not excessively hygroscopic or sticky supplement amino acid whose content should be standardizable. The animal feed supplement is based on a fermentation broth and contains the predominant proportion of its contents, optionally with the exclusion of part of the biomass. The biomass is preferably present in an amount of at most 10% by weight in the dry state. Proteins are preferably present in a maximum amount of 10% by weight. For the production, the sugar content is adjusted to a maximum of 4 g/l during fermentation, at least towards the end thereof, and at least part of the biomass is optionally removed during the working up.

16 Claims, No Drawings

ANIMAL FEED SUPPLEMENT BASED ON A FERMENTATION BROTH AMINO ACID, A PROCESS FOR ITS PRODUCTION AND ITS USE

The present invention relates to an animal feed supplement containing a high proportion of at least one amino acid, to a process for its production by fermentation and to its use.

BACKGROUND OF THE INVENTION

Animal feeds are supplemented with individual amino acids according to the needs of the animals. The supplements used in addition to chemically produced methionine include the fermentatively produced amino acids lysine, threonine and tryptophane. Thus in pigs, for example, the ratio of these three amino acids found to provide optimum feed utilization, i.e., minimum liquid manure production, is lysine:threonine:tryptophane=100%: 65%: 18%, taking lysine as 100% (see T. C. Wang, M. Fuller, British Journal of Nutrition, 62, 77–89 (1989).

Supplementing animal feeds e.g. with L-lysine has hitherto been carried out predominantly with L-lysine monohydrochloride having an L-lysine content of 80%. Since L-lysine is produced by fermentation, it is necessary to remove all other components of the crude fermentation broth by elaborate process steps before the L-lysine is converted into the monohydrochloride and the latter must then be crystallized.

Therefore, there has been no lack of attempts in the past to avoid the expensive process of preparing feed amino acids, in particular pure L-lysine monohydrochloride, and to convert the crude fermentation broth by a less expensive process into a solid animal feed. None of these experiments, however, has provided an economically acceptable result. Simple dewatering of the crude fermentation broth resulted in a highly hygroscopic, sticky concentrate which could not be used as an animal feed. For obtaining a pourable and storage stable product, it was necessary to incorporate a large quantity of a wide variety of additives in the concentrate, but this reduced the concentration of amino acid, which in many cases was already low.

Published European Patent application EP-B 122 163 discloses a process by which a crude fermentation broth, which can be dried to a solid and stable product, can be obtained if special fermentation conditions are observed. This product is obtained by dewatering the whole fermentation broth, but the L-lysine content of the product is only 35 to 48 percent by weight, which is considerably lower than that of L-lysine monohydrochloride. The biomass left in the product in this case acts as an additive which improves the free-flowing character of the product.

SUMMARY OF THE INVENTION

The object of the present invention is to provide an animal feed supplement which contains at least one amino acid at a high concentration with only a small proportion of unwanted by-products. A further object of the invention is to provide a supplement which is inexpensive to prepare and not excessively hygroscopic or sticky as end product. A still further object of the invention is to provide a supplement in which it is possible to standardize the amino acid content by simple means.

Other objects of the invention are to provide a process for the preparation of an animal feed supplement having the foregoing characteristics and using that animal feed supplement for feeding domestic animals.

These and other objects are achieved in an amino acid animal feed supplement based on fermentation broth which still contains most of the contents of the fermentation broth except for at least part of the biomass. Preferably, the dry mass of the supplement has the following composition:

| | |
|---|---|
| Amino acid(s) | 40–90% by weight |
| Proteins max. | 10% by weight |
| Carboxylic acids having less than 8 carbon atoms max. | 8% by weight |
| Total sugar max. | 10% by weight |
| Fats and oils max. | 5% by weight |
| Mineral substances | 3–30% by weight. |

In addition to containing the fermentatively obtained amino acid(s), the amino acid feed supplement according to the invention still contains a predominant proportion of the contents of the fermentation broth excluding at least part of the biomass and generally also the products which can be separated mechanically. The amino acid(s) content is preferably at least 40% by weight in the dry substance.

Another animal feed supplement according to the invention based on fermentation broth amino acid may alternatively or in addition have the following composition of the dry mass:

| | |
|---|---|
| Free amino acid(s) | 40 to 90 percent by weight |
| Proteins | maximum 10 percent by weight |
| Carboxylic acids having less than 8 carbon atoms | maximum 8 percent by weight |
| Total sugar | maximum 10 percent by weight |
| Fats and oils | maximum 5 percent by weight |
| Mineral substances | 3 to 30 percent by weight. |

This product still contains a major proportion of the contents of the fermentation broth, possibly with the exception of at least part of the biomass or of the mechanically separable products.

The product normally has a residual water content of at least 0.5% by weight, but the water content should not exceed 5% by weight in order to avoid the formation of lumps.

The protein content is determined from the total nitrogen content minus the inorganic nitrogen content, minus the nitrogen content of the free amino acids multiplied by 6.25 ((total N %—inorg. N %—AS N %)×6.25). The total nitrogen content is determined by Kjeldahl's decomposition method (standard process), the inorganic nitrogen content (ammonium content) may be determined e.g. colorimetrically, titrimetrically or potentiometrically and the nitrogen content of the free amino acid is determined by quantitative determination of the free amino acids (amino acid analyzer (ASA)) followed by calculation of the N content. The mineral substances are the total amount of all inorganic cations and anions.

Basic amino acids are present in the form of salts and therefore have a higher minimum mineral content (in the crude product at least 10%) and a lower maximum free amino acid content (in the crude product maximum 72%, in particular maximum 67%). The maximum value is determined by the anion (e.g. $SO_4^{2-}$; $Cl^-$); in the case of basic amino acids, 90% of the theoretical amount of free amount of acid base may generally be calculated as the salt (Example: (lys)$_2$. H$_2$SO$_4$ contains 75% by weight of lys. and a corresponding product according to the invention contains a maximum of 75×0.9=67.5% by weight of lys). The content also depends on the microorganisms used and the fermentation media.

In accordance with the invention, high amino acid contents of up to 90% in the dry state may be obtained, for example, in the production of threonine with *Escherichia coli* BKIIM B-3996 (FR-A 26 40 640), in particular by virtue of the relatively simple media used in this case.

In the production of lysine or tryptophane with *Corynebacterium glutamicum* or *Escherichia coli* K12-derivatives, the amino acid content in the crude product is somewhat lower; in the case of tryptophane, in particular, maximum fermentatively produced amino acid contents of 70% by weight are at typically present.

As used herein, the term "based on fermentation broth amino acid" means that at least part (preferably the predominant part) of the supplement consists of the dry mass of a fermentation broth with the exception of substances which are removable by mechanical separation techniques, which may have been removed according to the invention.

The mechanically removable substances include in particular the biomass and proteins. Mechanical separation techniques include in particular filtration (e.g. ultra- and microfiltration) and separation (e.g. centrifugation and decanting), by which, on the whole, only undissolved and/or relatively high molecular weight substances are removed.

The invention thus includes animal feed supplements, which, in addition to containing one or more amino acids, still contain most of the contents of the fermentation broth belonging to the amino acid(s), with the exclusion of at least part of the biomass. The invention also includes animal feed supplements conforming to the above composition which may contain all or part or none of the biomass. Especially when at least part of the biomass is still present in the supplement, the microorganisms are preferably natural microorganisms, i.e. microorganisms which have not been subjected to gene manipulation and are not subject to the German Gene Technology Act.

The supplements according to the invention may be obtained directly, e.g. by (spray) drying of a fermentation broth optionally preceded by separation of at least part of the biomass. It is surprising and particularly advantageous that the supplements may be produced with a protein content which is lower than that in previously known products (obtained from fermentation broths) and yet can be worked up into an easily handled powder or granulate (by drying).

When very pure fermentations are carried out (with only small residues of organic substances), the broth may even be dried to an easily handled granulate without the biomass and substantially without auxiliary substances such as additional (mineral) carriers. Moreover, fermentation broths which, from the start, are treated in such a way that they only contain little biomass may be dried directly (substantially without auxiliary substances such as additional (mineral) carriers) to produce the supplement. Both methods lead to the protein reduced or low protein supplements according to the invention. Known products always contain large quantities of biomass and in many cases also considerable quantities of other carriers.

The protein content of the supplement is very important and should not exceed 10% by weight and is preferably less than 10% by weight, in particular at most 7% by weight. Protein contents below 5% by weight are particularly preferred. In the interest of reducing the cost of the process, the protein content is in most cases at least 0.5%, generally 1% by weight or more. One reason why a low protein content is particularly important is that the supplement should, as far as possible, not increase the nitrogen or protein content of the mixed feed. Even a reduction in the N content of 0.05% is significant. The need for the supplement and the N-content of the liquid manure increase and the percentage of supplement amino acid(s) in the product decreases with increasing protein content of the feed, thereby increasing inter alia the freight costs, based on the supplement content.

Liquid manure may cause serious environmental problems. Further, a high protein content must be taken into account in the protein analysis. It is therefore desirable to introduce as little as possible unnecessary protein and protein of unknown composition into the mixed feed.

The fermentation broth normally contains more than 10-20% by weight of biomass in the dried substance. If the protein content in the animal feed supplement becomes too high, the proportion of fermentation biomass in the supplement is reduced and is preferably limited to a maximum of 10% by weight in the dry substance. The maximum proportion of fermentation biomass is frequently 5% by weight. Supplement compositions which are free from biomass, i.e. contain not more than 0.1% by weight of biomass, are preferred.

The supplement preferably contains on the whole only one amino acid.

Such a supplement is universally suitable as an addition to any feed or premix, according to its amino acid content. In certain feed mixtures, however, it may be advantageous to use a supplement containing several amino acids in a particular ratio to one another so that only one supplement need be used to provide the desired amino acid supplementation. The ratio of these amino acids may be obtained, for example, by mixing several amino acid fermentation broths or supplements (containing all or some or none of the biomass) or by the measured addition of small quantities of pure amino acid (e.g. tryptophane and/or threonine, for example in a lysine supplement).

Suitable amino acids for the present invention are in particular lysine, threonine, tryptophane and leucine, isoleucine, valine, proline and alanine.

Apart from containing a single amino acid or several specified amino acids in predetermined quantities, the supplement should be as free as possible from other amino acids which are undetermined or not suitable for feed supplementation.

The supplement amino acids should amount to at least 95% by weight of the total quantity of free amino acids in the supplement, preferably not less than 97% by weight. To reduce the cost of the process, the lower limit of the other α-amino acids which are not taken into account in the supplement or not determined (undefined) is in many cases 0.5% by weight, normally not less than 1% by weight. These other amino acids have similar disadvantages to the peptide content but can be more easily determined in a total amino acid analysis.

The sum of the other α-amino acids and proteins should preferably not exceed 11% by weight and is usually less than 11% by weight, in particular 8% by weight or less. The lower limit is normally 2% by weight.

The quantities given for proteins and amino acids or their sums are so small that these proportions need not be taken into account in the protein/amino acid analysis of the feed to be supplemented.

Higher values may in some cases impair the optimum amino acid composition required to be introduced with the supplement.

The total sugar content includes sugars which can be utilized by the microorganisms and those which cannot be utilized by them. Preferably the total sugar content is at most 5% by weight. Values of 2.5% by weight and less are particularly advantageous and the best values are 1.5% by weight and less. The higher the sugar content, the more hygroscopic is the product liable to be and the greater its tendency to be sticky. If the sugar contents are too high, evaporation and drying may be accompanied by the formation of Maillard products which reduce the yield and impair the properties of the product. The sugar content may be lowered by restricting the supply of sugar at least towards the end of fermentation.

The proportion of fats and oils is preferably limited as a rule to 3% by weight. As in the case of proteins, their proportion should be sufficiently low that they can be ignored in the supplementation of the mixed feed.

Supplements containing at least 49.5% by weight, preferably 50% or more of the desired free amino acid(s) are particularly suitable. The upper limit is preferably 60% by weight in the case of basic amino acids to keep the cost of the process down, and values of not more than 57% by weight have been found to be particularly suitable. For neutral amino acids, these values are 85% by weight and 80% by weight, respectively.

The supplements may be used in the form obtained by (spray) drying of the fermentation broth (optionally with reduced biomass) or they may be used as mixtures of such supplements (or of the broths) or together with other additives as premixes such as trace element-/vitamin premixes or mineral premixes.

Compared with pure isolation and compared with the products hitherto obtained from fermentation broths, such supplements are less expensive at high concentrations, can easily be standardized, are relatively free from by-products and are inexpensive to produce.

The supplement composition described is suitable in particular for lysine supplementation since lysine is easily available by fermentation and is one of the most important supplement amino acids.

The animal feed according to the invention is in most cases a light beige to brownish beige powder having a bulk density of from 0.4 to 0.7 kg/l. If L-lysine is present, this is bound in salt form, for example as sulphate or carbonate. It is completely stable and no reduction in the L-lysine content can be found after a storage time of more than 12 months at 25° C. Its hygroscopicity is good.

The product is freely pourable, does not tend to form lumps and can easily be incorporated homogeneously in full feeds or premixes. It also has excellent stability as a component of such mixtures.

As a source of L-lysine, it is at least as effective as the pure L-lysine monohydrochloride normally used, for the same L-lysine content in the feed.

The invention further relates to processes for the preparation of these animal feed supplements. The processes are characterized in that a microorganism producing at least one amino acid is cultivated in a fermentation medium containing at least one source of carbon, at least one source of nitrogen, mineral salts and trace elements. Fermentation is carried out under such conditions that the crude fermentation broth finally obtained has a utilizable sugar content of at most 4 g/l and in particular a solids content of from 7.5 to 26 percent by weight, an amino acid content of from 1–20 percent by weight, preferably from 4 to 10.5 percent by weight, and a sugar content of at most 2.6 percent by weight. Alternatively, fermentation may be carried out (optionally with a suitable microorganism) in such a manner that the biomass content is limited so that the dry mass of the fermentation broth contains at most 10% by weight of protein and in particular 40–90% by weight of amino acid(s), a maximum of 8% by weight of carboxylic acids having less than 8 carbon atoms, a maximum of 10% by weight of total sugar, a maximum of 5% by weight of fats and oils and a maximum of 5–30% by weight of mineral substances; the biomass may advantageously be reduced at least partly, preferably at the end of fermentation, in particular to a maximum of 10% by weight in the dry substance, and/or the microorganisms which form the biomass and optionally other substances are preferably removed by mechanical separation techniques after termination of the fermentation while most of the remaining components of the fermentation broth are left in the broth. These methods may be combined. The broth finally remaining is advantageously dried. Drying is advantageously carried out by condensing the remaining broth to a solids content of from 40 to 60% by weight and drying this viscous broth, e.g. by spray drying. If no biomass is to be removed, fermentation should be carried out under such conditions that as little biomass as possible is produced and the added nutrients should, at the end, have been consumed as much as possible. Such a fermentation is described, for example, in Published German Patent Application DE-A 41 30 867, Example 3.

The fermentation is preferably carried out under such conditions that the concentration of utilizable sugar in the fermentation broth is at most 0.3% by weight during at least 30% and preferably more than 70% of the total fermentation time.

The utilizable sugar content is adjusted to a maximum of 1 g/l towards the end of fermentation, i.e. no sugar is added and fermentation is stopped only when the sugar content is equal to or below this value. The fermentation residue is normally dried to a water content of at most 5% by weight after removal of at least part of the biomass.

The biomass may advantageously be completely removed. The end product obtained in that case contains a particularly high proportion of lysine base or other amino acids. In addition, the product obtained by complete removal of the biomass is particularly suitable for standardizing an end product to a constant amino acid content. This is necessary in particular when differing amino acid contents are obtained in individual fermentation batches.

The amino acid-producing microorganisms used for lysine are preferably suitable mutants of the species Corynebacterium or Brevibacterium, e.g. the freely available strain deposited under the number DSM 5715 at the German Collection for Microorganisms. The sources of carbon used are preferably starch hydrolyzates (glucose) or saccharose. A small proportion may also be derived from sugar beet or sugar cane molasses. This proportion should not exceed 5% by weight of the total source of carbon (10% by weight of molasses in the total carbon source).

For threonine and tryptophane, suitable mutants of the species *Escherichia coli* are preferably used, e.g. the strain BKIIM B-3996 (FR-A 2 640 640) for threonine.

The sources of nitrogen used, apart from ammonia and ammonium sulphate, are preferably substances containing hydrolyzates of protein, such as maize gluten, soya meal or the biomass from a previous batch. Corn-steep liquor and fish peptone are also suitable sources of nitrogen.

The fermentation temperature is suitably from 30° to 40° C. and the pH of the fermentation medium from 6.0 to 8.0. The fermentation time is preferably at most 100 hours.

After fermentation, the microorganisms may be killed by heat or by other processes, for example by the addition of a mineral acid, e.g. sulphuric acid. Part of the biomass is optionally subsequently removed by known processes such as separation, decanting or a combination of separation and decanting, ultrafiltration or microfiltration. The broth from which the biomass has been at least partly removed is then condensed by known processes, e.g. in a thin layer or falling film evaporator, to form a preconcentrate having a solids content of from 40 to 60 percent by weight. Final drying of the preconcentrate may be carried out by means of, for example, a spray drier, a spin flash drier or a fluidized bed drier.

The biomass which has been separated may be hydrolyzed easily by means of sulphuric acid, hydrochloric acid or suitable enzymes. The hydrolyzate thus obtained may advantageously be added as source of nitrogen to the fermentation medium of a subsequent fermentation. This recycling of biomass saves raw materials.

If the animal feed according to the invention is required to be standardized for its amino acid content, in particular the L-lysine content, this may be carried out by, for example, suitable choice of the quantity of biomass left in the product and/or suitable mixing of the preconcentrates from different fermentation broths. These preconcentrates are particularly suitable if they contain no biomass as they are then homogeneous.

Broths which are free from biomass or reduced in their biomass content may be mixed with original broths for standardization. Alternatively, small quantities of additives regarded by law as harmless in animal feeds may be added, for example wheat gluten or meal from the corn cob. A combination of the various steps may also be carried out.

DETAILED DESCRIPTION OF PREFERRED EMBODIMENTS

The following Examples serve to illustrate the invention in more detail:

EXAMPLE 1

150 kg of a sterile solution having the following composition are introduced into a fermentation vessel equipped with a stirrer and a ventilating system:

| | |
|---|---|
| Water | 130 liters |
| Glucose | 12.4 kg |

| -continued | |
|---|---|
| Maize gluten hydrolyzate, acidified with sulphuric acid | 9.0 kg |
| Ammonium sulphate | 1.5 kg |
| Mineral salts and Trace elements | 0.4 kg |
| adjusted to pH 7.5 with ammonia solution. | |

12 Liters of an inoculum of a Corynebacterium grown in the same fermentation medium but in a separate fermentation container were added to this solution at 33° to 35° C.

77 Liters of a sterile solution which had the following composition before neutralization to pH 7.5 were added within 40 hours:

| | |
|---|---|
| Water | 38 liters |
| Glucose | 40.0 kg |
| Maize gluten hydrolyzate, acidified with sulphuric acid | 8.3 kg |
| Ammonium sulphate | 0.9 kg |
| Defoamant (Nalco ®) | 0.08 kg |
| Mineral salts and Trace elements | 0.2 kg |

The pH was maintained at 7.0–7.5 by means of an ammonia solution during the whole fermentation period. The speed of the stirrer was adjusted to 600 revs/min and the ventilation rate to 0.5–0.7 vvm.

275 kg of a crude fermentation broth having a solids content of 34.1 kg, an L-lysine base content of 15.5 kg and a sugar content of 0.71 kg were obtained at the end of the fermentation period. The microorganisms were killed by heat and separated by a combination of separator and decanter.

The broth liberated from biomass was thickened to a solids content of about 52% by weight in a falling film evaporator at reduced pressure.

This preconcentrate was then dewatered in a spray drier to a light brownish beige powder having a bulk density of 0.51 kg/l and the following composition:

| | |
|---|---|
| L-lysine base | 52.1 percent by weight |
| other α-amino acids | 2.5 percent by weight |
| Proteins | 8.8 percent by weight |
| Carboxylic acids having less than 8 carbon atoms | 6.8 percent by weight |
| Sugar | 2.4 percent by weight |
| Fats and oils | 2.5 percent by weight |
| Mineral substances | 21.1 percent by weight |
| Water | 1.6 percent by weight. |

EXAMPLE 2

Fermentation was carried out as in Example 1 except that a mixture of 3.5 kg of sulphuric acid maize gluten hydrolyzate and 13.8 kg of sulphuric acid hydrolyzate of the biomass removed in Example 1 was used instead of the pure sulphuric acid maize gluten hydrolyzate.

272 kg of a crude fermentation broth having a solids content of 36.2 kg and containing 17.1 kg of L-lysine base and 0.55 kg of sugar were obtained at the end of the fermentation period.

The biomass was separated by ultra-filtration (<300,000 Dalton) without a preliminary treatment. The broth liberated from the biomass was condensed to a solids content of about 53 percent by weight as in Example 1.

Part of this preconcentrate was then dewatered in a fluidized bed drier to form a light brownish beige powder having a bulk density of 0.53 kg/l and the following composition:

| L-Lysine base | 62.1 percent by weight |
|---|---|
| other -amino acids | 1.2 percent by weight |
| Proteins | 2.6 percent by weight |
| Carboxylic acids having less than 8 carbon atoms | 3.1 percent by weight |
| Sugar | 2.0 percent by weight |
| Fats and oils | 1.7 percent by weight |
| Mineral substances | 24.4 percent by weight |
| Water | 1.6 percent by weight. |

Maize meal was added in such an amount to another part of the preconcentrate before it had been dewatered in a fluidized bed drier that the solid product obtained contained a standardized amount of L-lysine base of 60 percent by weight.

EXAMPLE 3

150 kg of a sterile solution having the following composition were introduced into a fermentation vessel equipped with stirrer and ventilating system:

| Water | 133.0 kg |
|---|---|
| Molasses | 0.77 kg |
| Saccharose | 3.68 kg |
| Maize gluten hydrolyzate, acidified with sulphuric acid | 1.03 kg |
| Biomass hydrolyzate, acidified with sulphuric acid | 9.4 kg |
| Ammonium sulphate | 1.3 kg |
| Mineral salts and Trace elements | 0.4 kg |
| adjusted to pH 7.5 with an ammonia solution. | |

17.6 Liters of an inoculum of a Corynebacterium of Strain No. DSM 5715 which had been grown in the same fermentation medium but in a separate fermentation container were added to this solution at 33° to 35° C. The strain is freely available from the German Collection for Microorganisms.

78 Liters of a sterile solution which had the following composition before neutralization to pH 7.5 were added within 39 hours:

| Water | 36 kg |
|---|---|
| Molasses | 2.7 kg |
| Saccharose | 43.1 kg |
| Maize gluten hydrolyzate, acidified with sulphuric acid | 1.1 kg |
| Biomass hydrolyzate, acidified with sulphuric acid | 10.7 kg |
| Ammonium sulphate | 0.9 kg |
| Mineral salts and Trace elements | 0.2 kg |

The pH was maintained at 7.0-7.5 with an ammonia solution during the whole fermentation period. The speed of the stirrer was adjusted to 600 revs/min and the ventilating rate to 0.5-0.7 vvm.

218 kg of a crude fermentation broth having a solids content of 29.2 kg and containing 10.6 kg of L-lysine base and 1.4 kg of sugar were obtained at the end of the fermentation period. The microorganisms were killed by heat and separated by a combination of separator and decanter.

The broth freed from biomass was condensed to a solids content of about 52 percent by weight in a falling film evaporator at reduced pressure. This preconcentrate was then dewatered in a spray drier to produce a light brownish beige powder having a bulk density of 0.50 kg/l and the following composition:

| L-lysine base | 41.8% by weight |
|---|---|
| other -amino acids | 4.1% by weight |
| Proteins | 8.5% by weight |
| Carboxylic acids having less than 8 carbon atoms | 6.7% by weight |
| Sugar | 5.7% by weight |
| Fats and Oils | 2.8% by weight |
| Mineral substances | 25.6% by weight |
| Water | 3.0% by weight. |

EXAMPLE 4

6.6 kg of sterile solution having the following composition were introduced into a fermentation vessel equipped with stirrer and ventilating system:

| Water | 6.05 kg |
|---|---|
| Glucose | 150 g |
| Ammonium sulphate | 50 g |
| Mineral salts and Trace elements | 50 g |

The pH was adjusted to 6.5 with an ammonia solution (25%).

0.7 kg of an inoculum of an *Escherichia coil* K12 descendant which had been grown in the same fermentation medium but in a separate fermentation container were added to the above solution at 33° C.

1.7 kg of sterile solution having the following composition were added within 24 hours:

| Water | 0.6 kg |
|---|---|
| Glucose | 1.1 kg. |

The pH was maintained at 6.5 with ammonia solution during the whole fermentation period.

Several fermentation broths obtained as described above were combined at the end of the fermentation period and the biomass was removed by ultrafiltration (<300,000 Dalton).

The broth freed from biomass was dewatered in a freeze drier to a light brown powder having the following composition:

| L-Tryptophane | 46.0% by weight |
|---|---|
| Other -amino acids | 4.0% by weight |
| Proteins | 1.7% by weight |
| Carboxylic acids having less than 8 carbon atoms | 3.0% by weight |
| Sugar | 1.0% by weight |
| Mineral substances | 25.0% by weight |
| Water | 2.3% by weight |
| Unspecified | 17.0% by weight. |

EXAMPLE 5

A threonine animal feed supplement may be obtained as follows:

A fermentation broth containing 85 g/l of L-threonine is prepared by a method analogous to that described in Published French Patent Application FR-A 2 6.40 640 by cultivating the strain *Escherichia coli* BKIIM B-3996 in a fermentation medium.

The biomass is then separated by ultrafiltration from the gene technologically altered microorganism and the broth freed from biomass is dewatered in a suitable drier.

What is claimed is:

1. A pourable storage stable amino acid animal feed supplement obtained from a fermentation broth wherein the amino acid supplement 1) still contains most of the solids content of the fermentation broth, 2) has an amino acid content of at least 40% by weight in dry mass, and 3) contains up to 10% by weight protein in dry mass.

2. A pourable storage stable amino acid animal feed supplement obtained from a fermentation broth wherein the amino acid supplement 1) still contains most of the solids content of the fermentation broth, and 2) has the following dry mass composition:

| | |
|---|---|
| Amino acid(s) | 40-90% by weight |
| Proteins max. | 10% by weight |
| Carboxylic acids having less than 8 C atoms max. | 8% by weight |
| Total sugar max. | 10% by weight |
| Fats and oils max. | 5% by weight |
| Mineral substances | 3-30% by weight |
| Water content | 0.5-5% by weight. |

3. The pourable storage stable amino acid animal feed supplement according to either claims 1 or 2, wherein the amino acid content is 1) in an amount at least 49.5% by weight and 2) fermentatively produced.

4. The pourable storage stable amino acid animal feed supplement according to either claims 1 or 2, wherein the amino acid content is 1) in an amount which is at most 60% by weight in the case of basic amino acids or at most 85% by weight in the case of neutral amino acids and 2) fermentatively produced.

5. A process for the production of a pourable storage stable amino acid animal feed supplement based on fermentation broth, comprising essentially the following steps:
   a) cultivating a microorganism which produces at least one α-amino acid in a fermentation medium containing at least one source of carbon, at least one source of nitrogen, mineral salts and trace elements,
   b) controlling utilizable sugar concentration in the fermentation medium to a maximum of 0.3% by weight during at least 30% of the fermentation time, which results in a crude fermentation broth containing at most 4 g/l of utilizable sugar and from 1-20% by weight of amino acid(s) at the end of fermentation, and
   c) drying the crude fermentation broth to a water content of 5% or less by weight.

6. A pourable storage stable amino acid animal feed supplement obtained from the process of claim 5.

7. A process for the production of a pourable storage stable amino acid animal feed supplement based on fermentation broth, comprising essentially the following steps:
   a) cultivating a microorganism producing at least one α-amino acid in a fermentation medium containing at least one source of carbon, at least one source of nitrogen, mineral salts and trace elements,
   b) controlling utilizable sugar concentration in the fermentation medium to a maximum of 0.3% by weight during at least 30% of the fermentation time, which results in a crude fermentation broth containing at most 4 g/l of utilizable sugar and from 1-20% by weight of amino acid(s) at the end of fermentation,
   c) reducing the microbial biomass content while maintaining a predominant proportion of the remaining components of the fermentation broth, and
   d) drying the biomass reduced fermentation broth to a water content of 5% or less by weight.

8. A process according to claims 5 or 7, wherein the crude fermentation broth has a solids content of from 7.5 to 26% by weight.

9. A process according to claims 5 or 7, wherein drying involves fluidized bed drying, spray drying or spin flash drying.

10. A process according to claims 5 or 7, wherein drying is spray drying.

11. A process according to claim 7, wherein reducing involves decanting, ultrafiltration or microfiltration.

12. A pourable storage stable amino acid animal feed supplement obtained from the process of claim 7.

13. A pourable storage stable amino acid animal feed supplement wherein the amino acid supplement 1) still contains most of the solids content of the fermentation broth, 2) has an amino acid(s) content of at least 40% by weight in dry mass, 3) contains up to 10% by weight protein in dry mass, and 4) is obtained by directly drying a fermentation broth which results from the cultivation of an α-amino acid producing microorganism in a fermentation broth under controlled conditions wherein the concentration of utilizable sugar in the fermentation medium was kept to a maximum of 0.3% by weight during at least 30% of the fermentation time.

14. A pourable storage stable amino acid animal feed supplement having a water content less than 5% by weight, having the following composition of dry mass:

| | |
|---|---|
| Amino acid(s) | 40-90% by weight |
| Proteins max. | 10% by weight |
| Carboxylic acids having less than 8 C atoms max. | 8% by weight |
| Total sugar max. | 10% by weight |
| Fats and oils max. | 5% by weight |
| Mineral substances | 3-30% by weight, | wherein the pourable storage stable amino acid feed supplement is obtained by directly drying a fermentation broth resulting from the cultivation of an α-amino acid producing microorganism in a fermentation medium under controlled conditions wherein the concentration of utilizable sugar in the fermentation medium is kept to a maximum of 0.3% by weight during at least 30% of the fermentation time, so that a crude fermentation broth containing at most 4 g/l of utilizable sugar is obtained at the end of fermentation and separation of the microbial biomass while leaving the predominant proportion of the remaining components in the crude broth.

15. A pourable storage stable amino acid animal feed supplement having a water content less than 5% by weight, having the following composition of the dry mass:

| | |
|---|---|
| Amino acid(s) | 40-90% by weight |
| Proteins max. | 10% by weight |
| Carboxylic acids having less than 8 C atoms max. | 8% by weight |
| Total sugar max. | 10% by weight |
| Fats and oils max. | 5% by weight |
| Mineral substances | 3-30% by weight. | wherein the pourable storage stable amino acid animal feed supplement is obtained from directly drying a fermentation broth which results from the cultivation of an α-amino acid producing microorganism in a fermentation medium under controlled conditions wherein the concentration of utilizable sugar in the fermentation medium is kept to a maximum of 0.3% by weight during at least 30% of the fermentation time which result in crude fermentation broth containing at most 4 g/l of utilizable sugar at the end of fermentation.

16. Animal feed or premix comprising the amino acid feed supplement according to one of the claims 1, 2, 6 and 12-15.

* * * * *